United States Patent
Davalian et al.

(10) Patent No.: US 8,870,847 B2
(45) Date of Patent: Oct. 28, 2014

(54) BLOOD VESSEL PERMEABILITY-ENHANCEMENT FOR THE TREATMENT OF VASCULAR DISEASES

(75) Inventors: Dariush Davalian, San Jose, CA (US); Stephen Pacetti, San Jose, CA (US); Florian Niklas Ludwig, Mountain View, CA (US); Syed Faiyaz Ahmed Hossainy, Fremont, CA (US); Irina Astafieva, Palo Alto, CA (US); Kimchi Tran, Milpitas, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 415 days.

(21) Appl. No.: 13/079,239

(22) Filed: Apr. 4, 2011

(65) Prior Publication Data

US 2011/0184384 A1 Jul. 28, 2011

Related U.S. Application Data

(63) Continuation of application No. 11/998,013, filed on Nov. 27, 2007, now abandoned.

(51) Int. Cl.
*A61M 31/00* (2006.01)
*A61L 31/16* (2006.01)
*A61L 29/16* (2006.01)
*A61M 25/00* (2006.01)
*A61M 25/10* (2013.01)
*A61F 2/95* (2013.01)

(52) U.S. Cl.
CPC ............ *A61L 29/16* (2013.01); *A61L 2300/62* (2013.01); *A61L 2300/416* (2013.01); *A61L 31/16* (2013.01); *A61M 25/0084* (2013.01); *A61M 25/104* (2013.01); *A61M 2025/105* (2013.01); *A61F 2/95* (2013.01)
USPC ........................................... 604/509

(58) Field of Classification Search
CPC .................... A61M 25/104; A61M 2025/105; A61L 2300/62; A61L 2300/622; A61L 2300/624; A61L 2300/626
USPC ........ 604/103.01, 103.02, 509; 606/191, 192, 606/194, 198; 424/422–426
See application file for complete search history.

(56) References Cited

U.S. PATENT DOCUMENTS

| 4,859,696 A | 8/1989 | Kamiya et al. |
| 5,873,852 A * | 2/1999 | Vigil et al. ..................... 604/509 |
| 6,663,880 B1 | 12/2003 | Roorda et al. |
| 2001/0051166 A1 | 12/2001 | Luo et al. |
| 2003/0125803 A1 | 7/2003 | Vallana et al. |
| 2003/0181856 A1 * | 9/2003 | Goldman ................. 604/103.01 |
| 2005/0129736 A1 | 6/2005 | Hunter et al. |
| 2006/0265043 A1 | 11/2006 | Mandrusov et al. |

OTHER PUBLICATIONS

Lorenceau et al., "Generation of Polymerosomes from Double-Emulsions", Longmuir vol. 21, pp. 9183-9186 (2005).
Miller "Breaking down Barriers" Science mag. vol. 297, pp. 1116-1118 (2002).
Neuwelt et al., "Osmotic Blood-Brain Barrier Disruption", J. Clin. Invest. The Am. Soc. for Clinical Investigation, vol. 64, pp. 684-688 (1979).
Pautot et al., "Production of Unilamellar Vesicles Using an Inverted Emulsion", Longmuir vol. 19, pp. 2870-2879 (2003).
Williams et al., "Rapid Restoration of Normal Endothelial Functions in Genetically Hyperlipidemic Mice by a Synthetic Mediator of Reverse Lipid Transport", Arterioscler. Thromb. Vas. Biol., pp. 1033-1039 (2000).

* cited by examiner

*Primary Examiner* — Kami A Bosworth
(74) *Attorney, Agent, or Firm* — Squire Patton Boggs (US) LLP

(57) ABSTRACT

This invention is directed to a method of treating a vascular disease involving administration to a patient by means of an angioplasty balloon a composition comprising a permeability-enhancing substance and a therapeutic agent.

9 Claims, No Drawings

BLOOD VESSEL PERMEABILITY-ENHANCEMENT FOR THE TREATMENT OF VASCULAR DISEASES

RELATED APPLICATIONS

This application is a continuation of application Ser. No. 11/998,013, filed 27 Nov. 2007, which is incorporated by references as if fully set forth herein.

FIELD

This application relates to the fields of chemistry, material science, medical devices and medicine. In particular it relates to a method of modulating the permeability of mammalian vessel membranes with regard to the administration of therapeutic agents.

BACKGROUND

In general, therapeutic agents for the treatment of various diseases are administered in one of two modalities: systemic or local. Systemic delivery involves the administration of a therapeutic agent at a discrete location remote from the afflicted locale, followed by dispersal of the agent throughout the patient's body including, of course, to the target site or organ. In order to insure that a therapeutically effective amount of the agent reaches the afflicted site, it is usually necessary to administer an initial dose substantially greater than the therapeutically effective amount to account for dilution the agent undergoes as it spreads throughout the body and loss of agent due to reaction with bodily components such as enzymes. Systemic delivery is carried out primarily in two ways: introduction of the therapeutic agent into the digestive tract (enteral administration) or into the vascular system (parenteral administration), either directly such as injection into a vein or an artery or indirectly such as injection into a muscle or into the bone marrow. Delivery by each of these routes is strongly influenced by the so-called ADMET factors: absorption, distribution, metabolism, excretion and toxicity. For enteric administration, such factors as a compound's solubility, its stability in the acidic environs of the stomach and its ability to permeate the intestinal wall all affect the extent to which the drug is absorbed and therefore its bioavailability. For parenteral delivery factors such as enzymatic degradation, the lipophilic/hydrophilic partitioning coefficient, protein binding, etc. will affect the bioavailability of an agent.

Local delivery comprises administration of the therapeutic agent at least proximally but preferably directly to the afflicted locale. The ADMET factors tend to be less important than with systemic administration since the agent is being delivered essentially directly to the treatment site. Thus, the initial dose can be at or very close to the therapeutically effective amount. With time, some of the locally delivered therapeutic agent may diffuse over a wider region but such is not the intent of localized delivery and the concentration of the diffused agent will ordinarily be sub-therapeutic, i.e., too low to have a beneficial effect.

While diffusion of a therapeutic agent affects both systemic and local delivery modalities, it is particularly troublesome with regard to localized delivery where the amount of therapeutic agent being delivered is often as close to the minimum effective concentration as possible to avoid secondary problems such as toxicity and other undesirable side effects. With regard to vascular disorders, the therapeutic agent must usually traverse the endothelium, a layer of cells that line the interior surface of all blood vessels, and all or a portion of the media if the agent is administered within the lumen of the vessel. If the agent is administered exterior to the vessel then it must traverse the periadventitia, adventitia, or a portion of the media to reach the targeted site. The rate at which the therapeutic agent penetrates into and ultimately traverses these tissue layers versus the rate at which the therapeutic agent is diffused away from the locale of interest determines how much of the agent must be administered in the first place.

What is needed with regard to the local treatment of vascular disorders is a method of increasing the rate of therapeutic agent traverse of the periadventitia/aventitia/media/endothelium so that less of the agent is lost during the treatment, thereby requiring less agent initially with a concomitant reduction in potential side effects and possibly cost. The current invention provides such a method.

SUMMARY

Thus, an aspect of this invention is a method of treating a vascular disease, comprising: providing a delivery device; advancing the delivery device to a locale of interest in a vessel of a patient; administering a permeability-enhancing composition to the locale of interest through the delivery device; and, administering a therapeutic agent to the locale of interest through the delivery device either as a component of the permeability-enhancing composition or concomitantly with but separately from the permeability-enhancing composition or subsequent to administration of the permeability-enhancing composition.

In an aspect of this invention administering the permeability-enhancing composition comprises bathing the locale of interest with a solution that is hyperosmolar in relation to endothelial cells at the locale.

In an aspect of this invention, the hyperosmolar solution comprises a solute selected from the group consisting of a biocompatible salt, a monosaccharide, a disaccharide, a water miscible biocompatible organic solvent, a water-soluble biocompatible small organic molecule, a water-soluble protein, a water-soluble peptide and a water-soluble biocompatible surfactant.

In an aspect of this invention, the solute comprises one or more compounds selected from the group consisting of water-soluble glucose, mannose, fructose, sucrose, trehalose, biocompatible halides, biocompatible phosphates, ethylene diamine tetraacetic acid, taurocholic acid, benzalkonium chloride, capric acid, melittin or an amino acid.

In an aspect of this invention, administering the permeability-enhancing composition comprises using a composition that physicochemically interacts with at least one component of endothelial cells or extracellular matrix.

In an aspect of this invention, the permeability-enhancing composition comprises a saponin, a semi-synthetic saponin, DS-1, DS-1(R), DS-2 or QH-957.

In an aspect of this invention, the permeability-enhancing composition comprises hyaluronidase, recombinant hyaluronidase or rHuPH20.

In an aspect of this invention, the permeability-enhancing composition comprises ethanol, propylene glycol, glycerol, N-methyl pyrrolidone, dimethylsulfoxide, xylene, nitric oxide or a nitric oxide generator.

In an aspect of this invention, the method herein further comprises a mechanical permeation enhancer.

In an aspect of this invention, the delivery device comprises a catheter.

In an aspect of this invention, the catheter is selected from the group consisting of a porous balloon catheter, a double-wall porous balloon catheter, and infusion catheter and a needle injection catheter.

In an aspect of this invention, the delivery device comprises an implantable medical device.

In an aspect of this invention, the implantable medical device comprises a stent.

In an aspect of this invention, the delivery device comprises an angioplasty balloon.

In an aspect of this invention, the delivery device comprises a hollow needle.

In an aspect of this invention, the therapeutic agent comprises a particulate carrier.

In an aspect of this invention, the particulate carrier comprises a nanoparticle, a micelle, a worm micelle, a liposome or a polymerosome.

In an aspect of this invention, the nanoparticle, micelle, worm micelle, liposome or polymerosome further comprises the permeability-enhancing composition.

In an aspect of this invention, the permeability enhancing composition independently comprises a separate nanoparticle, micelle, worm micelle, liposome or polymerosome.

In an aspect of this invention, the nanoparticle, micelle, worm micelle, liposome or polymerosome comprises a targeting component disposed on its surface and, further, the permeability-enhancing composition is likewise disposed on its surface.

In an aspect of this invention, the locale of interest comprises a site of an atherosclerotic lesion, a restenotic lesion, a suspected vulnerable plaque, a vulnerable plaque or a peripheral arterial lesion.

DESCRIPTION

Use of the singular herein includes the plural and visa versa unless expressly stated to be otherwise. That is, "a" and "the" is to be construed as referring to one or more of whatever the word modifies. As a non-limiting example, "a lubricious polymer" includes one such polymer, two polymers or, under the right circumstances, even more polymers unless it is expressly stated or is unambiguously obvious from the context that such is not intended. Likewise, "a solvent" may refer to a single solvent or a mixture of two or more solvents unless, again, it is expressly stated or obvious from the context that such is not intended.

As used herein, a "delivery device" refers to any manner of apparatus that is used or that may be used to reach a locale of interest in a vessel in a patient's body. The device may be transitory, that is, it may be a device that is inserted into a patient's body for only so long as is necessary to administer a permeability-enhancing composition and a therapeutic agent to a patient or it may be an implantable medical device intended to remain in a patient's body for longer than necessary to deliver the two components of this method, possibly for as long as the remaining lifetime of the patient. Intermediate between transitory devices and implantable medical devices intended to remain in place permanently are biodegradable implantable medical devices which over time degrade to substances that can either be adsorbed into or excreted by the body.

An example of a transitory delivery device is, without limitation, as simple a device as a hollow needle that can be inserted into a patient's body at or near a locale of interest in a vessel and through which the components of the method herein can be delivered. The needle may be inserted into the adventitia at the locale of interest or it may be inserted directly into the vascular lumen. An example, without limitation, of a transitory device is a vascular catheter.

Another non-limiting example of a transitory delivery device is a vascular catheter. A vascular catheter comprises a thin, flexible tube with a manipulating means at one end, referred to as the proximal end, which remains outside the patient's body, and an operative device at or near the other end, called the distal end, which is inserted into a patient's artery or vein. The catheter is often introduced into a patient's vasculature at a point remote from the locale of interest, e.g., into the femoral artery of the leg where the target is the heart. The catheter is steered, assisted by a guide wire than extends through a lumen in the flexible tube, to the target site whereupon the guide wire is withdrawn at which time the lumen may be used for the introduction of therapeutic agents to the locale of interest.

An "implantable medical device" refers to any type of appliance that is totally or partly introduced, surgically or medically, into a patient's body or by medical intervention into a natural orifice, and which is intended to remain there after the procedure. As noted above, the duration of implantation may be essentially permanent, i.e., intended to remain in place for the remaining lifespan of the patient; until the device biodegrades; or until it is physically removed.

Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, grafts, stent-grafts, artificial heart valves and cerebrospinal fluid shunts.

Further non-limiting examples of implantable medical devices are vessel wraps and stents. A vessel wrap is a thin sheet of flexible material, which may be fabric, polymer, metal, etc. that is literally wrapped around the outside of a vessel and is in contact with the outer surface. The wrap may be solid or it may be formed in virtually any manner of desired pattern such as, without limitation, a mesh, a ribbed polymeric structure or an embossed metal sheet.

A "stent" refers generally to any device used to hold tissue in place in a patient's body. Particularly useful stents, however, are those used for the maintenance of the patency of a vessel in a patient's body when the vessel is narrowed or closed due to diseases including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. A stent can be used in, without limitation, neuro, carotid, coronary, pulmonary, aorta, renal, biliary, iliac, femoral and popliteal arteries as well as other peripheral vasculatures. A stent can be used in the treatment or prevention of diseases such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents, including in particular those of this invention, may be employed for the delivery of therapeutic agents to specific treatment sites in a patient's body. In fact, therapeutic agent delivery may be the sole purpose of the stent or the stent may be primarily intended for another use such as those discussed above with drug delivery providing an ancillary benefit. Any stent design currently known or any that may be disclosed in the future that is directed at least in part to the delivery of therapeutic agents to locales of interest in a patient's body are within the scope of this invention.

As used herein, a "locale of interest" refers to a location within vessel of a patient that is the site of an atherosclerotic lesion or a location in the vessel where an atherosclerotic lesion may occur, a restenotic lesion or a location in the vessel where a restenotic lesion may occur, a known or suspected site of vulnerable plaque or a location in a peripheral vessel where a peripheral arterial disease has manifested itself.

As used herein, a "vessel of a patient" refers to any of the essentially tubular organ that transports blood in the mammalian body including arteries, arterioles, veins, venules and capillaries. Preferably at present the vessel of a patient refers to an artery.

A "patient" refers to any species that might benefit from treatment using the method herein but at present is preferably a mammal and most preferably a human being.

As used herein, "administering a permeability-enhancing composition" to a locale of interest refers to contacting the composition with the endothelium at the locale of interest if the delivery device is situated within the lumen of a vessel or with the periadventitia or adventitia if the delivery device is situated outside the vessel adjacent to a locale of interest situated within the vessel. The permeability-enhancing composition must be in contact with the endothelium, media, adventitia or (peri)adventitia for a sufficient duration such that the composition has time to have its intended effect, that is, to increase the permeability of the tissue at that locale.

While it is understood that the method of this invention is applicable to either the endothelium, media, the periadventitia or the adventitia, it is presently preferred that it be applied to permeability enhancement of endothelial tissue. Thus the remainder of this disclosure will be directed to the endothelium but it is understood that essentially the same technique will apply to the outer tissues of blood vessels as well.

If the permeability-enhancing composition is intended to increase permeability by creating a hyperosmolar or hypertonic (q.v, below) environment at the locale of interest, the composition may be administered by simply suffusing the locale for a period of time before introducing a therapeutic agent to the site. If on the other hand, the composition is one that reacts with the constituents of the endothelial cells themselves or the constituents of the extracellular matrix (EM), then the composition may be administered much the same way as the therapeutic agent. That is, a previously determined effective amount of the composition is administered to the locale of interest either prior to or concomitant with administration of the therapeutic agent.

As used herein, "bathing" the locale of interest refers to supplying a sufficient amount of the hyperosmolar solution to the locale of interest so as to maintain the osmotic imbalance at the site for a sufficient duration for the efflux of water from the cells to take place to an extent sufficient to render the region between the cells, i.e., the region of the EM more penetrable to the therapeutic agent or particulate carrier administered concurrent with or subsequent to the bathing step. Since blood is constantly flowing through the vasculature this may require a constant stream of the hyperosmolar solution directed to the endothelium at the locale of interest so as to create the osmotic imbalance. It may be beneficial to temporarily block the vessel either proximal to the locale of interest (as determined from the direction of blood flow, the side closest to the heart being proximal) or both proximal and distal to the locale of interest, in this latter case thereby creating a compartment that can be flooded with the hyperosmolar solution. In this latter instance a bolus of the hyperosmolar may be administered.

As used herein, "administering a therapeutic agent to the locale of interest" refers to contacting a therapeutically effective amount of the therapeutic agent or particulate carrier containing the therapeutic agent with the endothelium. While it may be possible to contact the therapeutic agent with the periadventitia, adventitia, or media and have it traverse the additional tissue to reach the endothelium, at present it is preferred that the therapeutic agent be administered from inside the vessel, i.e., through the lumen of the vessel, such that it can be placed in immediate intimate contact with the endothelium. A "therapeutically effective amount" refers to that quantity of the therapeutic agent that has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutically effective amount includes a prophylactically effective amount, which is that amount of the therapeutic agent that has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, "permeability" refers to the degree to which a therapeutic agent or particulate carrier containing a therapeutic agent is able to traverse the endothelial layer and gain access to the sub-structure within.

"Permeability-enhancing," as the term itself suggests, refers to the ability of a composition to increase the ease with which the therapeutic agent or particulate carrier crosses the endothelium as measured by the percentage of an administered amount that is found on the side of endothelium away from the lumen, either totally or per unit time.

As used herein, a "permeability-enhancing composition" refers to one or more substances, which may be neat or in solution, which alone or in combination are capable of increasing the permeability of the endothelium of a blood vessel. For the purposes of this invention, being "capable of increasing the permeability of the endothelium" may be as simple as increasing the solute concentration outside the endothelial cells such that a osmotic imbalance is created resulting in water effluxing out of the cells thereby causing the cells to collapse or it may mean actually reacting with a constituent of the endothelial cells or the EM.

For the purposes of this invention, permeability of the endothelium can be increased by two mechanisms. One mechanism involves creating a hyperosmotic, hyperosmolar or hypertonic (the terms are interchangeable) environment at the locale of interest. In a hyperosmotic environment, the solute concentration outside a cell is higher than the solute concentration within the cell resulting in the creation of an osmotic imbalance. Due to this imbalance there will be a net flow of water from the lower concentration environment to the higher concentration environment as the system naturally attempts to reestablish an isotonic condition where there is no net flow of water into or out of the cells. In the hyperosmotic environment created by an embodiment of this invention, water flows out of the cells causing the cells to at least partially collapse, preferably not to the point of permanently damaging the cells, thereby increasing the distance between cells and stretching, at some points perhaps even pulling apart, the EM. Therapeutic agents administered to the locale of interest will then be able to more easily filter between the endothelial cells and access the region beyond wherein lies the actual target of the therapeutic agent.

The second means of increasing the permeability of the endothelium involves physicochemical interaction between the composition and components of the endothelial cells themselves or between the composition and components of the EM. An example, without limitation, of a composition that interacts with endothelial cell components is the saponins.

Saponins are glycosides of plant origin. They contain either a steroid, alkaloid steroid or triterpenoid aglycone to which one or more sugar chains are attached. The sugars are usually glucose, galactose, glucuronic acid, xylose or rhamnose although others are known to occur in certain saponins. The saponins directly affect cell permeability by reversibly interacting with the outer cell membrane including forming pores therein. It has been reported that it is the number of sugar side chains on a given saponin that most influences its permeability-enhancing capabilities although contradictory reports also exist. The different conclusions may be the result of the particular type of cell used in the study. Since the actual mode of action is not pertinent to this invention, without being bound to any particular theory it appears that the permeability enhancing capabilities of saponins may be related to a combination of target membrane composition, the type of saponin side chain(s) and the nature of the aglycone. In any event, those skilled in the art will be able, based on this disclosure, to select appropriate saponins for use in the method of this invention.

Of the myriad known saponins, presently preferred for the purposes of this invention are saponins extracted from *Quillaja saponaria*, a member of the Rosaceae family. The *Quillaja saponins* consist of a triterpene with surgar side chains on carbons 2 and 28. Variation in the sugar side chain give rise to at least 50 different types of *Quillaja saponins*.

In addition to the naturally-occurring *Quillaja saponins*, semi-synthetic derivatives can also be used in the methods of this invention. As should be obvious given the diversity of structure in the saponins themselves, the number of possible structures of semi-synthetic saponins is legion and all such compounds are within the scope of this invention. In particular, however, the semi-synthetic saponins known as DS-1, DS-1(R), DS-2 and QH-957 are presently preferred for use in the methods of this invention. DS-1 and DS-2 are the result of mild alkaline hydrolysis of acyl groups on the saponin. DS-1 and DS-2 are more hydrophilic than the parent compound. Reduction of an aldehyde group of DS-1 affords DS-1(R). Removal of the fucose-containing oligosaccharide of DS-1 gives QH-957.

An example of a composition that reacts with components of the EM rather than components of the endothelial cells themselves is hyaluronidase. The EM is composed of an interlocking mesh of fibrous proteins and glycosaminoglycans (GAGs). GAGs are carbohydrate polymers that attach themselves to the fibrous proteins of the EM to form proteoglycans. Among the proteoglycans involved in EM formation are heparin sulfate, chondroitin sulfate and keratan sulfate. The EM also contains non-proteoglycan components, in particular hyaluronic acid or hyaluronan. Hyaluronan is a non-sulfonated polysaccharide GAG consisting of alternating residues of D-glucouronic acid and N-acetylglucosamine. It is widely distributed throughout connective, endothelial and neural tissues. Hyaluronan is one of the chief components of the EM, in fact it as been estimated that a 150 lb human has roughly 15 grams of hyaluronan in his/her body.

Hyaluronidase is an enzyme that hydrolyzes hyaluronan, by cleaving the glucosaminidic bond between C1 of the acetylglucosamine and the C4 of glucouronic acid, the two constituents of hyaluronic acid. This results in a temporary decrease in the viscosity of the EM which facilitates the movement of transudates and exudates such as therapeutic agents past the endothelial layer.

Naturally-occurring hyaluronidases constitute a group of neutral or acid active enzymes that occur throughout the animal kingdom and that vary with respect to substrate specificity and mechanisms of action. Of primary import to this invention are the mammalian hyaluronidases (EC 3.2.1.35), which are endo-β-N-acetylhexoaminidases that afford tetrasaccharides and hexasaccharides as the major end products of hydrolysis. The hyaluronidases have both hydrolytic and transglycosidase activity and can degrade hyaluronan and chrondroitin sulfates, another consitutent of the EM.

In addition to naturally-occurring hyaluronidase, recombinant hyaluronidases that maintain the ability to cleave hyaluronan, be it by the same mechanism or a different one, are also within the contemplation of this invention. "Recombinant" simply means that the hyaluronidase so-designated is created (expressed) by an artificial gene, one that does not occur in nature. Presently preferred is a recombinant human hyaluronidase known as rHuPH20, available from Halozyme Theraputics, Inc., San Diego, Calif. PH-20 is a widely conserved mammalian glycosylphosphatidyl-inositol-anchored spermatozoa surface protein well-known for its hyalouronidase activity. Native human hyaluronidase HuPH20, is reported to be a 509 residue protein, a truncated version (residues 36-482, inclusive) of which constitutes the recombinant form, rHuPH20.

As used herein, a "therapeutic agent" refers to, without limitation, an anti-restenosis agent, an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist, an antioxidant, or any combination thereof.

Examples of antiproliferative agents include, without limitation, actinomycins, taxol, docetaxel, paclitaxel, rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, everolimus, Biolimus A9 (Biosensors International, Singapore), deforolimus, AP23572 (Ariad Pharmaceuticals), perfenidone and derivatives, analogs, prodrugs, co-drugs and combinations of any of the foregoing.

Examples of anti-inflammatory agents include both steroidal and non-steroidal (NSAID) anti-inflammatory agents such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus and derivatives, analogs, prodrugs, co-drugs and combinations of any of the foregoing.

Examples of antineoplastics and antimitotics include, without limitation, paclitaxel, docetaxel, methotrexate, azathioprine, vincristine, vinblastine, fluorouracil, doxorubicin hydrochloride, and mitomycin.

Examples of antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä, calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, 4-amino-2,2,6,6-tetramethylpiperidine-1-oxyl (4-amino-TEMPO) and derivatives, analogs, prodrugs, codrugs and combinations thereof.

Examples of cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of antiallergic agents include, without limitation, permirolast potassium.

Other compounds that may be used as bioactive agents of this invention include, without limitation, alpha-interferon, genetically engineered endothelial cells, dexamethasone, antisense molecules which bind to complementary DNA to inhibit transcription, and ribozymes, antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and derivatives, analogs, prodrugs, codrugs and combinations of any of the foregoing.

Other bioactive agents include a corticosteroid, everolimus, zotarolimus, sirolimus, and derivatives thereof, paclitaxel, biolimus A9, a bisphosphonate, ApoA1, a mutated ApoA1, ApoA1 milano, an ApoA1 mimetic peptide, an ABC A1 agonist, an anti-inflammatory agent, an anti-proliferative agent, an anti-angiogenic agent, a matrix metalloproteinase inhibitor and a tissue inhibitor of metalloproteinase.

As used herein, "biocompatible" refers to a substance that, both in its native pure state and as any decomposition products that might be generated from it, is not, or at least is minimally, toxic to living tissue; does not, or at least minimally and reparably, injure(s) living tissue; and/or does not, or at least minimally and/or controllably, cause(s) an immunological reaction in living tissue. With regard to salts, both the cation and anion must be biocompatible. Examples of generally biocompatible cations are, without limitation, sodium ($Na^+$), potassium ($K^+$), calcium ($Ca^+$), magnesium ($Mg^{++}$), iron ($Fe^{+++}$) and ammonium ($NH_4^+$). Others are well-known to those skilled in the art.

As used herein, "water-miscible" refers to an organic liquid that combines with water to form a clear, homogenous mixture at the concentrations required for the purposes of this invention. That amount will be easily determinable by those skilled in the art based on the disclosures herein with regard to the teaching that the desired result is a hyperosmotic environment in the vicinity of the endothelium.

As used herein, "water-soluble" refers to a solid, which may be inorganic or organic, that forms a clear, homogenous mixture when place in water at the concentrations required for the purposes of this invention.

"Homogenous" merely means that the resultant mixture is sufficiently uniform that a sample taken from any point in the mixture has the same composition as a sample taken from any other point in the mixture.

As used herein, an "amino acid" refers to any organic acid, i.e., a molecule with a —COOH functional group also containing an α-amino (—$NH_2$) group; however at present it is preferred that the amino acids be selected from the group commonly known as the standard amino acids or sometimes the proteinogenic amino acids because they are encoded by the normal genetic code. There currently are 20 standard amino acids: alanine, arginine, asparagine, aspartic acid, cysteine, glutamic acid, glutamine, glycine, histidine, isoleucine, leucine, lysine, methionine, phenyl alanine, proline, serine, threonine, tryptophan, tyrosine and valine. Relatively recently selenoadenine has been found to be incorporated into a number of proteins and is included with the above as a useful amino acid for the purposes of this invention. In naturally-occurring biological proteins, these amino acids exist primarily as l- or d-enantiomers but for the purposes of this invention they may be used as their l- or d-enantiomers or as racemic mixtures.

As used herein a "peptide" refers a short polymer formed by the linking together of α-amino acids through the formation of amide bonds, sometimes referred to as peptide bonds. A protein, on the other hand, refers to a substantially longer polymer comprised of poly(peptides). There is no exact dividing line between a peptide and a protein and such is not essential to this invention. Therefore, for the purposes of this invention a peptide refers to a poly(amino acid) of up to 50 amino acids while above 50 amino acids the compound will be considered a protein.

As used herein, a "surfactant" refers to an amphiphilic (having both hydrophobic groups (their "tails") and hydrophilic groups (their "heads")) organic molecule that is soluble both in organic solvents and in water. They operate by reducing the surface tension between two materials, which may be liquid-gas, liquid-liquid or liquid-solid. For the purposes of the method of this invention their primary purpose is creating a hyperosmotic environment in the vicinity of the endothelium and secondarily to further ease the transfer of therapeutic agents or particulate carriers through the endothelium by reducing surface tensions between the agent/particle and the components of the EM.

As used herein, "physiochemically interacting" refers to the situation where a permeability-enhancing composition actually reacts with and changes a component of the EM or an endothelial cell as opposed to the situation where the composition merely creates a hyperosmolar condition in the vicinity of the endothelium at the locale of interest. Examples of such physicochemical interactions are described above with regard to saponins (physiochemically interact with endothelial cell outer membrane) and rHuPH20 (physiochemically interact with hyaluronan). Other such permeability-enhancing compositions useful in the method herein will become apparent to those skilled in the art based on the disclosure herein and are within the scope of this invention.

As used herein, a "vascular disease" refers to a disease of the blood vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease.

"Atherosclerosis" or an "atherosclerotic lesion" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting is strokes, if the afflicted artery is a carotid artery, heart attack if the artery is a coronary artery or loss of organ function if the artery is peripheral.

"Restenosis" or a "restenotic lesion" refers to the re-narrowing or blockage of an artery at or near the where angioplasty or other surgical procedure was previously performed to remove a stenosis. It is usually due to smooth muscle cell proliferation at times accompanied by thrombosis. Prior to the advent of implantable stents to maintain the patency of vessels opened by angioplasty, restenosis occurred in 40-50% of patients within 3 to 6 months of undergoing the procedure. Post-angioplasty restenosis before stents was due primarily to neointimal hyperplasia and vasospasm, with smaller rates of dissection and thrombosis or blood-clotting at the site of the procedure. Stent placement essentially eliminates vasospasm and dissections. However, the stented sites are still susceptible to restenosis due to neointimal hyperplasia and abnormal tissue growth at the site of implantation. While the use of IIb-IIIa anti-platelet drugs such as abciximab and epifabatide, which are anti-thrombotic, reduced the occurrence of post-procedure clotting with stents (although stent placement itself can initiate thrombosis. Restenosis tends also to occur at 3 to 6 months after stent placement, but it is not reduced by the use of anti-clotting drugs. Thus, alternative therapies are continuously being sought to mitigate, preferably eliminate, this type of restenosis. Drug eluting stents (DES) which release a variety of therapeutic agents at the site of stent placement have been in use for some time and it is to improved drug-delivery of DESS that this invention is at least in part directed.

"Vulnerable plaque" refers to an atheromatous plaque that has the potential of causing a thrombotic event and is usually characterized by a very thin wall separating a lipid filled, necrotic core from the lumen of an artery. The thinness of the wall renders the plaque susceptible to rupture. When the plaque ruptures, the inner core of lipid-rich plaque is exposed to blood where it has the potential of causing a fatal thrombotic event through adhesion and activation of platelets and plasma proteins to components of the exposed plaque.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect the presence of vulnerable plaque in the arterial wall. After death, an autopsy can reveal the ruptured plaque in the arterial wall. However, the pre-rupture narrowing of these palques cannot typically be seen with commonly available medical imaging. Thus, for the purposes of this invention, it may be beneficial to treat a locale of interest where a vulnerable plaque is suspected to be present based on the symptomology at the locale even though the plaque has not been expressly observed.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage derived enzymatic degradation can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

Peripheral vascular diseases are generally caused by structural changes in blood vessels caused by such conditions as inflammation, hyperlipidemia, diabetes, and tissue damage. A subset of peripheral vascular disease is peripheral artery disease (PAD) or equivalently herein a peripheral arterial lesion. PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet.

As used herein, "late stent thrombosis" refers to the formation of blood clots in the vicinity of an implanted stent long after—months, even years—the stent was in place. It has been hypothesized that the formation of blood clots may be due to delayed healing resulting from the use of cytostatic drugs.

As used herein "hollow needle" simply refers generally to the well-known thin, elongate, tubular device having a tapered point that is used to inject therapeutic agents into various parts of the body including without limitation subcutaneously although the shape of the needle itself for the purposes of this invention may be configured in ways that are not usually seen with regard to syringes. Such alternate configurations are well-known to those skilled in the art.

As used herein, a "particulate carrier" refers to a biocompatible, generally non-therapeutic substance within which a therapeutic agent and/or a permeability-enhancing composition can be encapsulated or to the surface of which either or both may be adhered. Examples of particulate carriers useful for the purposes of this invention are, without limitation, nanoparticles, micelles, worm micelles, liposomes and polymersomes.

As used herein, a "nanoparticle" refers to a solid particle having as its largest trans-sectional, i.e., as measured through the particle as opposed to along its surface, dimension of no greater than 500 nanometers, preferably 250 nanometers and most preferably at present no greater than 200 nanometers. The solid can have an desired shape although substantially spherical particles are well-known in the art, are readily prepared and are presently preferred. By "substantially spherical" is meant that the particles need not have a surface that mimics a table tennis ball, i.e., virtually perfectly spherical but rather may by odd-shaped but would be considered generally "round" by one of skill in the art. The nanoparticle may be constructed of one or more biocompatible substances and may be porous so as to permit elution of a therapeutic substance embedded in it or may be biodegradable such that as it degrades the therapeutic substance is released into the environment.

A micelle is a spherical colloidal nanoparticle spontaneous formed by many amphiphilic molecules in an aqueous medium when the Critical Micelle Concentration (CMC) is exceeded. Amphiphilic molecules have two distinct components, differing in their affinity for a solute, most particularly water. The part of the molecule that has an affinity for water, a polar solute, is said to be hydrophilic. The part of the molecule that has an affinity for non-polar solutes such as hydrocarbons is said to be hydrophobic. When amphiphilic molecules are placed in water, the hydrophilic moiety seeks to interact with the water while the hydrophobic moiety seeks to avoid the water. To accomplish this, the hydrophilic moiety remains in the water while the hydrophobic moiety is held above the surface of the water in the air or in a non-polar, non-miscible liquid floating on the water. The presence of this layer of molecules at the water's surface disrupts the cohesive energy at the surface and lowers surface tension. Amphiphilic molecules that have this effect are known as "surfactants." Only so many surfactant molecules can align as just described at the water/air or water/hydrocarbon interface. When the interface becomes so crowded with surfactant molecules that no more can fit in, i.e., when the CMC is reached, any remaining surfactant molecules will form into spheres with the hydrophilic ends of the molecules facing out, that is, in contact with the water forming the micelle corona and with the hydrophobic "tails" facing toward the center of the of the sphere. Therapeutic agents suspended in the aqueous medium can be entrapped and solubilized in the hydrophobic center of micelles which can result in an increase in the bioavailability as well as improving the stability in biological surroundings, improving the pharmacokinetics and possibly decreasing the toxicity of the therapeutic agent. In addition because of their nanoscale size, generally from about 5 nm to about 50 nm, micelles have been shown to exhibit spontaneous accumulation in pathological areas with leaky vasculature and impaired lymphatic drainage, a phenomenon known as the Enhanced Permeability and Retention or EPR effect.

The problem with micelles formed from relatively low molecular weight surfactants is that their CMC is usually quite high so that the formed micelles dissociate rather rapidly upon dilution, i.e., the surfactant molecules dissolve, and the concentration of micelles drops with the resulting precipitation of the therapeutic agent. Fortunately, this short-coming can be avoided by using lipids with a long fatty acid chain or two fatty acid chains, specifically phospholipids and sphingolipids, or polymers, specifically block copolymers to form the micelles.

Polymeric micelles have been prepared that exhibit CMOs as low as $10^{-6}$ M (molar). Thus, they tend to be very stable while at the same time showing the same beneficial characteristics as surfactant micelles. Since micelles are nano-scale particles, they may be administered using the porous balloon discussed above as well as in polymeric matrices. Examples of micelle-forming polymers are, without limitation, methoxy poly(ethylene glycol)-b-poly($\epsilon$-caprolactone), conjugates of poly(ethylene glycol) with phosphatidylethanolamine, poly(ethylene glycol)-b-polyesters, poly(ethylene glycol)-b-poly(L-aminoacids), poly(N-vinylpyrrolidone)-bl-poly(orthoesters), poly(N-vinyl pyrrolidone)-b-polyanhydrides and poly(N-vinylpyrrolidone)-b-poly(alkyl acrylates).

In addition to the classical spherical micelles described above, therapeutic agents may be delivered using the methods of this invention in compositions comprising synthetic worm micelles. Worm micelles, as the name suggests, are cylindrical in shape rather than spherical. They are prepared by varying the weight fraction of the hydrophilic polymer block to the total block copolymer molecular weight in the hydrophilic polymer-b-hydrophobic polymer structure discussed above for preparing spherical micelles. Worm micelles have the potential advantage of not only being bio-inert and stable as are spherical polymeric micelles but also of being flexible. Polyethylene oxide has been used extensively to create worm micelles with a number of hydrophobic polymers such as, without limitation, poly(lactic acid), poly(ε-caprolactone), poly(ethylethylene) and poly(butadiene). A representative description of worm micelle formation, characterization and drug loading can be found in Kim, Y., et al., *Nanotechnology*, 2005, 16:S484-S491. The techniques described there as well as any other that is currently known or may become known in the future may be used in the regional delivery method of this invention.

Somewhat more complex than micelles but likewise useful in the method of this invention are liposomes, particles comprised of a phospholipid bilayer that encloses an air-filled or hydrophilic liquid core.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, know as a phospholipid bilayer or a lamella, converge into a sphere and in doing so entrap some of the aqueous medium, and whatever may be dissolved or suspended in it, in the core of the sphere. Examples of phospholipids that may be used to create liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)]sodium salt, 1,2-dimyristoyl-sn-glycero-3-[phospho-L-serine]sodium salt, 1,2-dioleoyl-sn-glycero-3-phosphoethanolamine-N-glutaryl sodium salt and 1,1',2,2'-tetramyristoyl cardiolipin ammonium salt.

Liposomes may be unilamellar, composed of a single bilayer, or they may be multilamellar, composed of two or more concentric bilayers. Liposomes range from about 20-100 nm diameter for small unilamellar vesicles (SUVs), about 100-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of therapeutic agent entrapped tends to be rather low, typically in the range of a few percent. Recently, however, liposome preparation by emulsion templating (Pautot, et al., *Langmuir*, 2003, 19:2870) has been shown to result in the entrapment of virtually 100% of aqueous solute. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids. Liposomes comprising phospho- and/or sphingolipids may be used to deliver hydrophilic (water-soluble) or precipitated therapeutic compounds encapsulated within the inner liposomal volume and/or to deliver hydrophobic therapeutic agents dispersed within the hydrophobic core of the bilayer membrane.

It has been reported that large unilamellar liposomes alone, that is, absent of any additional therapeutic agent, when administered in large amounts intravenously may stimulate reverse cholesterol transport and may have anti-atherogenic effects similar to that of HDL (Williams, K. J., et al., *Arterioscler. Thromb. Vasc. Biol.*, 2000, 20:1033-39). While further evaluation is necessary, if such is proven to be the case, administration of large liposomes without added therapeutic agent using the delivery interface of this invention may provide a beneficial effect on patients known or suspected to be afflicted with a vascular disease.

The diblock copolymers discussed above with regard to micelle formation can be further modified to form bilayer structures similar to liposomes. The structures are referred to as polymersomes. Depending on the length and chemical nature of the polymers in the diblock copolymer, polymersomes can be substantially more robust that liposomes. In addition, the ability to control completely the chemical nature of each block of the diblock copolymer permits tuning of the polymerosome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

Polymersomes can be prepared in the same manner as liposomes. That is, a film of the diblock copolymer can be formed by dissolving the copolymer in an organic solvent, applying a film of the copolymer-containing solvent to a vessel surface, removing the solvent to leave a film of the copolymer and then hydrating the film. This procedure, however, tends to result in a polydisperse population of micelles, worm micelles and vesicles of varying sizes. Polymersomes can also be prepared by dissolving the diblock copolymer in a solvent and then adding a poor solvent for one of the blocks, which will result in the spontaneous formation of polymersomes.

As with liposomes, polymersomes can be used to encapsulate therapeutic agents by including the therapeutic agent in the water used to rehydrate the copolymer film. Polymersomes can also be force-loaded by osmotically driving the therapeutic agent into the core of the vesicle. Also as with liposomes, the loading efficiency is generally low. Recently, however, a technique has been reported that provides polymersomes of relative monodispersivity and high loading efficiency (Lorenceau, et al., *Generation of Polymersomes From Double Emulsions, Langmuir*, 2005, 21:9183-86). The technique involves the use of microfluidic technology to generate double emulsions consisting of water droplets surrounded by a layer of organic solvent. These droplet-in-a-drop structures are then dispersed in a continuous water phase. The diblock copolymer is dissolved in the organic solvent and self-assembles into proto-polymersomes on the concentric interfaces of the double emulsion. The actual polymersomes are formed by completely evaporating the organic solvent from the shell. By this procedure the size of the polymersomes can be finely controlled and, in addition, the ability to maintain complete separation of the internal fluids from the external fluid throughout the process allows extremely efficient encapsulation.

When it is stated that a permeability-enhancing composition "independently comprises a separate" particulate carrier from that comprising a therapeutic agent, what is meant is that the permeability-enhancing composition not only is encapsulated in a separate particulate carrier but that carrier may be different from that containing the therapeutic agent. For example, without limitation, the therapeutic agent may be encapsulated in a liposome while the permeability-enhancing composition may be encapsulated within, or adhered to the surface of, a nanoparticle, a micelle, a worm micelle or a polymersome.

As used herein, a "targeting component" refers to a molecular entity that has a particular affinity for another molecular entity such that if the second entity is present at a locale of interest, the first entity, when it encounters the second entity, will interact with the second entity and thereupon be immobilized at the locale. An example of targeting is the affinity of an antibody for an antigen. If a particular antigen is responsible for the diseased condition of a locale of interest and therefore is present at the locale, it would be possible to bind a therapeutic agent or a particular carrier to an antibody to that antigen in such a manner that the binding affinity of the antibody for the antigen is not affected and then to administer the carrier antibody to the patient. When the antibody encounters the antigen, it will bind to the antigen and be immobilized. The therapeutic agent can then interact with the antigen. Another example of targeting is the affinity of a ligand for a receptor expressed on a cell's surface. If the receptor is unique to the locale of interest due, for instance, to its relationship to the disease at the locale, a highly localized, disease specific treatment may be possible. Specific examples of such targeting entities include, without limitation, are antibodies to CD34, RGD, YIGSR, peptides and antibodies to IIbIIIa, heparin, hyaluronic acid, laminin, collagen, ICAM-1, ICAM-2, ICAM-3, fibrinogen, fibronectin, vitronectin, thrombospondin, osteopontin, integrins, VCAM-1, N-CAM, PECAM-1, IgCAM, folate, oligonucleotide aptamers, selectins, and cadherins. Other targeting entities will be apparent to those skilled in the art based on this disclosure; all such targeting entities are within the scope of this invention.

Nitric oxide (chemical formula NO) is a gaseous signaling molecule that plays a role in a host of biological processes. Also known as "endothelium-derived relaxing factor," NO is used by the endothelium lining of blood vessels to signal surrounding smooth muscle cells to relax, causing the vessel to dilate. As a result of this dilation, the cells of the endothelium are pulled away from one another and the EM between the cells is stretched and rendered more permeable. Thus NO may be used to accomplish an objective of this invention, enhanced permeation of the endothelium.

As used herein, a "nitric oxide generator" refers to a molecule that under physiological conditions releases NO. Examples of in vivo NO generators include, without limitation, S-nitrosocysteine, S-nitroso-N-acetylpenicillamine and sodium nitroprusside.

As used herein, a "mechanical permeation enhancer" refers to a device that when operationally directed to the endothelium at the locale of interest causes an increase in the permeability of the endothelium at that site. Examples of mechanical permeation enhancing means include, without limitation, phonophoresis, sonophoresis, low intensity pulsed ultrasound stimulation (LIPUS), iontophoresis and pressure pulse generation.

While the current invention has been described with regard to certain embodiments it is understood that those skilled in the art will, based on this disclosure, be able to devise, without undue experimentation, other embodiments not expressly set forth herein. All such embodiments are nevertheless within the scope of this invention.

What is claimed:

1. A method of treating a vascular disease, comprising:
providing a delivery device comprising an angioplasty balloon;
advancing the balloon to a locale of interest in a vessel of a patient;
administering a permeability-enhancing composition from the balloon to the locale of interest targeting a site cross the endothelium, wherein:
the permeability-enhancing composition is selected from the group consisting of hyaluronidase, recombinant hyaluronidase (rHuPH20), a saponin, a semisynthetic saponin, DS-1, DS-1(R), DS-2 or QH-957; and
a therapeutic agent comprising a particulate carrier is administered as a component of the permeability-enhancing composition or concomitantly with but separately from the permeability-enhancing composition.

2. The method of claim 1, wherein the delivery device further comprises a catheter.

3. The method of claim 2, wherein the catheter is selected from the group consisting of a porous balloon catheter and a double-wall porous balloon catheter.

4. The method of claim 1, wherein the particulate carrier comprises a nanoparticle, a micelle, a worm micelle, a liposome or a polymersome.

5. The method of claim 4, wherein the nanoparticle, micelle, worm micelle, liposome or polymersome further comprises the permeability-enhancing composition.

6. The method of claim 5, wherein the nanoparticle, micelle, worm micelle, liposome or polymersome further comprises a targeting component disposed on its surface and, further, the permeability-enhancing composition is likewise disposed on its surface.

7. The method of claim 4, wherein the permeability enhancing composition independently comprises a separate particulate carrier from that the therapeutic agent comprises, the particulate carrier being independently selected from the group consisting of a nanoparticle, a micelle, a worm micelle, a liposome or a polymersome.

8. The method of claim 4, wherein the nanoparticle, micelle, worm micelle, liposome or polymersome further comprises a targeting component disposed on its surface and, further, the permeability-enhancing composition is likewise disposed on its surface.

9. The method of claim 1, wherein the locale of interest comprises an atherosclerotic lesion, a restenotic lesion, a suspected vulnerable plaque, a vulnerable plaque or a peripheral arterial lesion.

* * * * *